(12) United States Patent
Kerechanin, II et al.

(10) Patent No.: US 7,032,589 B2
(45) Date of Patent: Apr. 25, 2006

(54) PORTABLE VENTILATOR

(75) Inventors: Charles W. Kerechanin, II, Burtonsville, MD (US); Dexter G. Smith, Columbia, MD (US); Jennifer A. Nix, Ellicott City, MD (US); Protagoras N. Cutchis, Highland, MD (US)

(73) Assignee: The Johns Hopkins University, Baltimore, MD (US)

( * ) Notice: Subject to any disclaimer, the term of this patent is extended or adjusted under 35 U.S.C. 154(b) by 424 days.

(21) Appl. No.: 10/349,628

(22) Filed: Jan. 23, 2003

(65) Prior Publication Data

US 2003/0172931 A1 Sep. 18, 2003

Related U.S. Application Data

(60) Provisional application No. 60/351,077, filed on Jan. 23, 2002.

(51) Int. Cl.
*A61M 15/00* (2006.01)
*A62B 7/00* (2006.01)
*F01N 7/08* (2006.01)
*F01D 25/04* (2006.01)
*F04B 39/00* (2006.01)

(52) U.S. Cl. .................. 128/200.24; 128/204.21; 128/204.26; 181/403; 181/248; 415/119; 417/312

(58) Field of Classification Search ............. 181/403, 181/60, 248, 483, 231; 128/205.18, 202.12, 128/204.18, 204.26, 201.25, 200.24, 204.21; 415/119; 417/312
See application file for complete search history.

(56) References Cited

U.S. PATENT DOCUMENTS

| | | | | |
|---|---|---|---|---|
| 4,080,103 A | * | 3/1978 | Bird | 417/3 |
| 4,127,123 A | * | 11/1978 | Bird | 128/204.25 |
| 4,342,573 A | * | 8/1982 | McCombs et al. | 96/109 |
| 4,493,614 A | * | 1/1985 | Chu et al. | 417/22 |
| 4,794,922 A | * | 1/1989 | DeVries | 128/204.18 |
| 4,870,961 A | | 10/1989 | Barnard | 128/202.27 |
| 5,163,902 A | * | 11/1992 | Lynn et al. | 604/86 |
| 5,357,946 A | | 10/1994 | Kee et al. | 128/200.24 |
| 5,664,594 A | | 9/1997 | Kee | 134/22 |
| 6,155,257 A | * | 12/2000 | Lurie et al. | 128/204.23 |
| 6,526,970 B1 | * | 3/2003 | DeVries et al. | 128/204.21 |
| 6,547,851 B1 | * | 4/2003 | Warren | 95/21 |
| 2003/0051454 A1 | * | 3/2003 | Yeung | 55/467.1 |
| 2003/0140922 A1 | * | 7/2003 | Dunlop | 128/203.12 |

OTHER PUBLICATIONS

Beranek, Leo L., "Noise Reduction" 1960, MCGraw-Hill, pp. 414-433.*
Surface Temperature of Two Portable Ventilators During Simulated Use under Clinical Conditions, Military Medicine, vol. 166, Oct. 2001, Lt. Col. Paul N. Austin, USAF et al.

* cited by examiner

*Primary Examiner*—Henry Bennett
*Assistant Examiner*—Dinnatia Doster-Greene
(74) *Attorney, Agent, or Firm*—Albert J. Fasulo, II (57) ABSTRACT

A portable ventilator for providing an air-recipient with compulsory respiration is provided with an outlet manifold and a single-expansion-chamber muffler configured so that airflow through an inhale outlet port of the muffler is pulse-free and a transmission loss, defined as the ratio of sound power generated by the at least one compressor and incident on the muffler to the sound power transmitted by the muffler, is sufficient to deaden the sound power of the compressor.

23 Claims, 8 Drawing Sheets

PORTABLE VENTILATOR

CROSS-REFERENCE TO RELATED APPLICATIONS

This application claims priority to U.S. Provisional Application No. 60/351,077, filed Jan. 23, 2002. The contents of the aforesaid U.S. Provisional Application No. 60/351,077 are incorporated by reference herein.

STATEMENT OF GOVERNMENTAL INTEREST

This invention was made with U.S. Government support under a contract with the U.S. Army Medical Research and Material Command, no. DAMD17-99-2-9041. The U.S. Government has certain rights in the invention.

BACKGROUND OF THE INVENTION

1. Field of the Invention

The present invention generally relates to a battery operated portable apparatus configured to provide respiratory ventilation in the far forward early trauma scene as well as in the clinical setting. Particularly, the invention is directed to a manifold/muffler assembly of a portable ventilator configured to provide smooth, constant airflow to the air recipient and to reduce the noise level associated with the cyclically operated compressor of the ventilator.

2. Description of Related Art

Respiration involves the introduction of gases, especially oxygen, to the lung during inspiration and the removal of waste gases, particularly carbon dioxide, during expiration. In healthy individuals respiration is normally effected by spontaneous ventilation or breathing, which results in the introduction of the necessary gases. Unfortunately, intentionally inflicted wounds or physiological and pathological processes may compromise normal pulmonary function leading to the inhibition of effective respiration or total respiratory failure. In such cases respiratory therapy, often involving artificial ventilation to some degree, is required.

For example, respiratory therapy is often necessary for victims of natural disasters or military actions associated with weapons of mass destruction, as well as for patients undergoing surgery or those suffering disorders and diseases of the pulmonary air passages. Typically, such respiratory therapy involves the use of mechanical ventilators.

Mechanical ventilators are simply devices that effect ventilation or, in other words, cause airflow into the lungs. More specifically, such devices typically force air into the lungs during the inspiration phase of the breathing cycle but allow a return to ambient pressure during spontaneous exhalation. The forced influx of fresh air by mechanical ventilation facilitates the pulmonary mediated processes that comprise respiration in mammals. One of these processes, the removal of waste gases, is the primary mechanism by which carbon dioxide is excreted from the body. Modern mechanical ventilators are designed to provide ventilation by regulating tidal volume (volume per breath), flow rate, delivery profile and respiratory flow thereby controlling carbon dioxide excretion. Because they can also regulate airway pressure and the concentration of inspired oxygen they offer control over oxygenation as well.

Numerous makes and models of mechanical ventilators are used today. All of the ventilators used are either volume-controlled ventilators or pressure-controlled ventilators. In the former, the ventilator is designed to deliver a set volume of gas regardless of the airway pressure. Such devices usually have a pressure cutoff to prevent damage to the lungs. In contrast, the pressure-controlled ventilators, based on the selected respiratory rate, the inspiratory gas flow and the peak airway pressure, deliver inspired gas, while monitoring the tidal volume, until the desired pressure is reached. Each of these types of mechanical ventilators incorporates a number of sophisticated features, which allow unparalleled control over the delivery of gases to the lung. In order to meet the diverse needs of patients requiring ventilation therapy, common mechanical ventilators offer several ventilation modes, each having a variety of programmable parameters, offering an almost unlimited versatility. Accordingly, both types of the above-discussed ventilators are highly expensive to manufacture and maintain.

Exemplifying at least some of the above-discussed principles of operation is U.S. Pat. No. 4,794,922 which discloses a ventilator operating in clinical conditions and configured to have an electronically controlled artificial respiration to a patient. The ventilator, as disclosed, features an air-tight manifold configured to house a system of ducts which provide air communication between the source of gas and the patient. While meeting many structural requirements, the ventilator of U.S. Pat. No. 4,794,922 is powered by an external source and, therefore, is not portable. Further, because of the complexity of the overall structure, the device is difficult to manufacture and is expensive.

A battery powered air mover or ventilator is known using "unfiltered" air supplies which generate acoustic noise and are characterized by a pulsatile flow, both of which can be quite disturbing to the air recipient. Mainly, these disadvantages stem from an unsatisfactory design of the gas-conveying and gas-storing components and particularly, the complexity of the internal tubing and the excess of the connectors needed to assemble the known ventilators. Particularly troublesome noise in the known ventilators is generated by a compressor cycled on and off to provide for the inspiration and expiration of the air recipient's lungs. When turned on, the loud noise produced by the compressor travels through the ventilation circuit tube and is heard by the air recipient. Critically, the configuration of the gas-conveying ducts and accumulators renders airflow entering the air-recipient's lungs pulsed. In addition, the number of elbows and tee connectors along the air path is characterized by multiple contractions and expansions in the flow area. As a consequence, the connectors creates the flow noise, which in combination with the pulsation, detrimentally affects audible and tactile senses of the patient during breathing.

Accordingly, a need exists for a light and compact field-portable ventilator configured to provide a constant, smooth flow of air towards a recipient thereof with a reduced level of noise produced by a compressor, as well as by airflow, typically associated with a battery-powered ventilator.

SUMMARY OF THE INVENTION

To meet this need, the present invention provides for a field-portable ventilator configured to reduce the audible noise generated by at least one compressor and to provide a substantially uniform flow of compressed gas towards the air recipient.

To reduce the noise and flow pulsation, the inventive device includes a patient circuitry including a manifold and a muffler located downstream from the manifold along an output path of compressed air and being in flow communication therewith. Geometry of the manifold and muffler provides for smooth airflow through the outlet path and for decreases in the sound level at the downstream end of the respiratory or patient circuit due to the work of the compressor.

Further reduction of the audible components is achieved by the inventive device, which, in addition to the muffler in the patient circuitry, is advantageously configured to have another muffler located along an inlet path of air. The muffler positioned along the upstream portion of the flow path is configured to deaden the external noise emitted through the inlet port of the inventive device during actuation of a compressor.

Provision of the upstream and downstream mufflers, substantially reducing the audible components generated by the power-actuated components, such as compressors, does not amount to the overall enlargement of the inventive device. On the contrary, the device is miniaturized due to a reduced number of connectors needed to assemble the device. Accordingly, large numbers of the device can be easily delivered to the field when a great number of victims may be in need of compulsory respiration. Concomitantly, fewer components substantially lower the cost of the device, if compared to the known portable models of the air mover or ventilator.

The geometry of the inventive muffler is based on the analysis description provided in the following publication: Beranek, Leo L. (ed.) 1971, "Noise and Vibration Control", McGraw-Hill, Inc., New York, N.Y. This publication discloses how to design a single-expansion-chamber muffler by evaluating its Transmission Loss ($L_{TL}$). The Transmission Loss is defined as the ratio of sound power incident on the muffler to the sound power transmitted by the muffler, given in decibels. The Transmission loss can be calculated in terms of two parameters m and kl calculated according to the following:

$$L_{TL} = 10 \log \left[ 1 + \frac{1}{4} \left( m - \frac{1}{m} \right)^2 \sin^2 kl \right] \quad (1)$$

The parameter m is the ratio of the cross-sectional area of the chamber to the cross-sectional area of duct:

$$m = \frac{S_2}{S_1} \quad (2)$$

The parameter kl is given as a ratio of 2 pi times the length of the muffler divided by the wavelength according to the following:

$$kl = \frac{2\pi l}{\lambda} \quad (3)$$

λ is the wavelength of the sound at the frequency of interest and is calculated in terms of frequency (f) in Hz, and muffler temperature ($\theta_c$) in ° C. or muffler temperature ($\theta_f$) in ° F. according to the following:

$$\lambda = \frac{345}{f} \sqrt{\frac{\theta_c + 273}{295}} \text{ meters} \quad (4)$$

-continued $$\lambda = \frac{1130}{f} \sqrt{\frac{\theta_f + 460}{530}} \text{ feet} \quad (5)$$

Ideally, the inventive muffler would be less than about 3"×4" so as to minimize the space it takes up in the ventilator. The sound generated by the compressor inside of the ventilation tube has a frequency of about 200 Hz, with corresponding harmonics. Appendix A of the Beranek publication shows the Transmission Loss for mufflers having various lengths and diameters close to these ideal values.

In accordance with another aspect of the invention, the ventilator may produce increased flow output, if such is needed. Remarkably, the installation of the two-compressor power unit does not require structural modifications of the original structure, which remains light and space-efficient. While attempts at installing multiple compressors have been made in the past, the use of elbow and tee connectors with longer lengths of tubing, and coupling the compressors in parallel, caused "fighting" to occur between the compressors, due to lack of synchronous timing between the compressors. As a result, the desired output could not be achieved. The inventive system overcomes the "fighting" problem in a three-fold manner. First, the flow-conveying system configured in accordance with the invention, allows for the air to flow in "straight paths", by not requiring multiple bends to connect the compressors in parallel. This reduction in the numbers of elbow and tee connectors significantly reduces the restrictions seen by the flow through elimination of multiple contractions and expansions in the flow area. Secondly, the connectors used to attach the tubing to the manifold are sized so as to reduce or eliminate for aforementioned changes in the flow area. Thirdly, the tubing lengths are reduced by positioning the compressors in close proximity to the manifold and muffler, thereby reducing long lengths of tubing, which could further restrict the flow.

Accordingly, the inclusion of the muffler configured in accordance with the inventive field-portable ventilator substantially reduces the noise emitted through inlet and outlet ports of a ventilation circuit during the activation of the compressor. Still another advantage provides for constant, smooth airflow to an air recipient, which otherwise would have a pulsation in the flow detrimental to the air recipient. Yet a further advantage of the inventive device is the reduced complexity of the internal tubing.

It is, therefore, an object of the invention to provide a portable ventilator characterized by the reduced noise level during operation of its compressor on both the air input and output paths.

Yet a further object of the invention is to smooth the airflow for a constant output to the air recipient.

Still another object of the invention is to provide a portable ventilator configured to provide increased airflow from multiple compressors in a linear fashion while featuring a compact, light structure.

Still yet a further object of the present invention is to provide a kit for providing compulsory respiration to an air recipient, comprising a portable ventilator provided with:
at least one compressor operative to provide airflow towards the at least one air recipient,
spaced inlet and outlet manifold/muffler assemblies located along an air path and having each a single-chamber muffler and an inlet opening located upstream from and in direct flow communication with a respective single-chamber muffler, wherein the inlet and outlet manifold/muffler assemblies are configured to decrease an acoustic signal generated by the at least one compressor along upstream and downstream ends of the path and to provide smooth constant airflow to the air recipient; and a disposable air conveying tubing providing flow communication between the air recipient and the portable ventilator, the disposable air conveying tubing being externally attachable to an outlet port of the single-chamber muffler of the outlet manifold/muffler assembly and traversed by the smooth, constant airflow.

BRIEF DESCRIPTION OF THE DRAWINGS

The above and other objects, features and advantages will become more readily apparent from the detailed description of the preferred embodiment accompanied by the following drawings, in which.

DESCRIPTION OF THE PREFERRED EMBODIMENTS

Figures 1, 2:
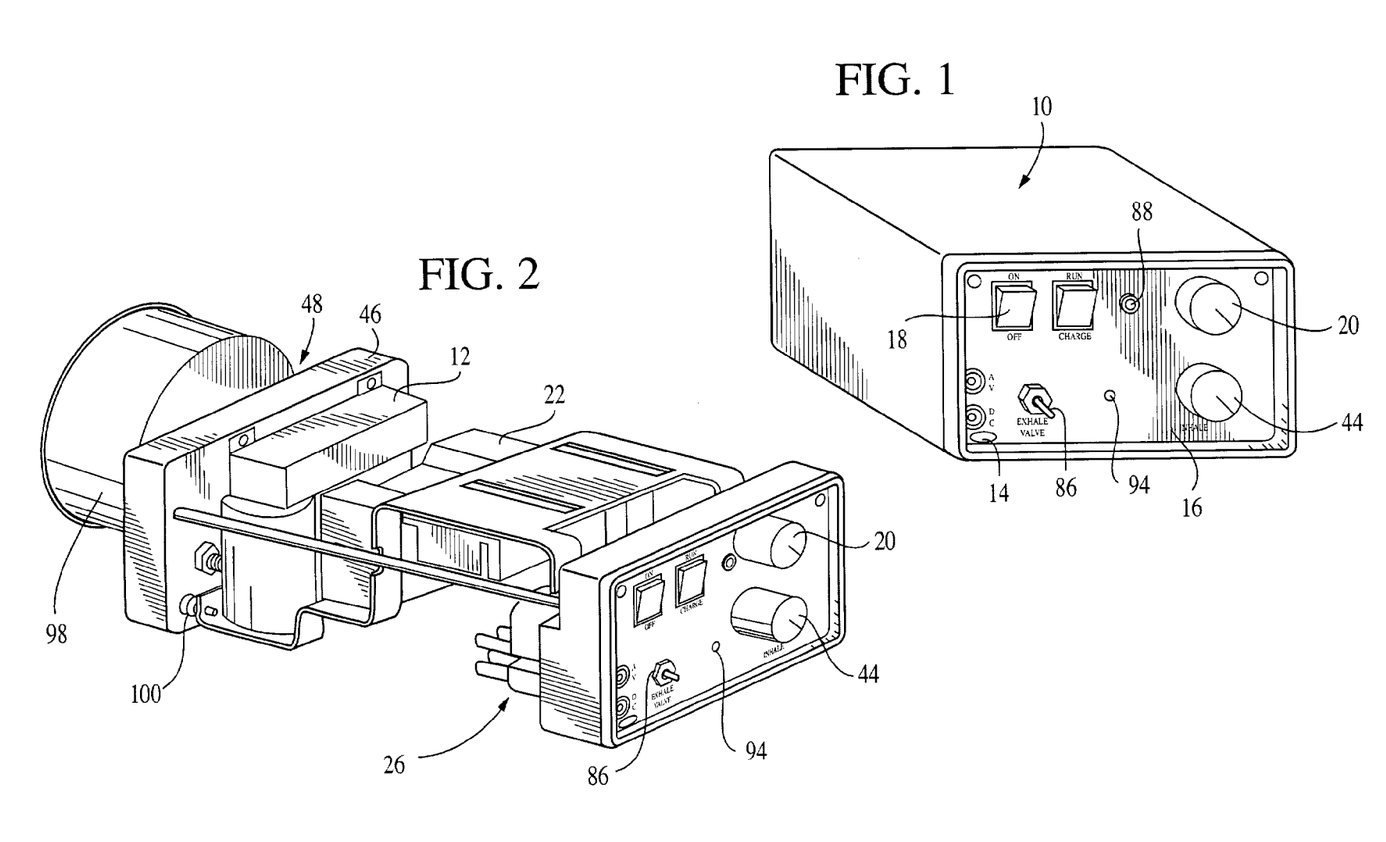
FIG. 1 is a perspective view of the device assembled in accordance with the present invention.
FIG. 2 is a top/side perspective view of the inventive device of FIG. 1 shown without its housing.
Figure 3:
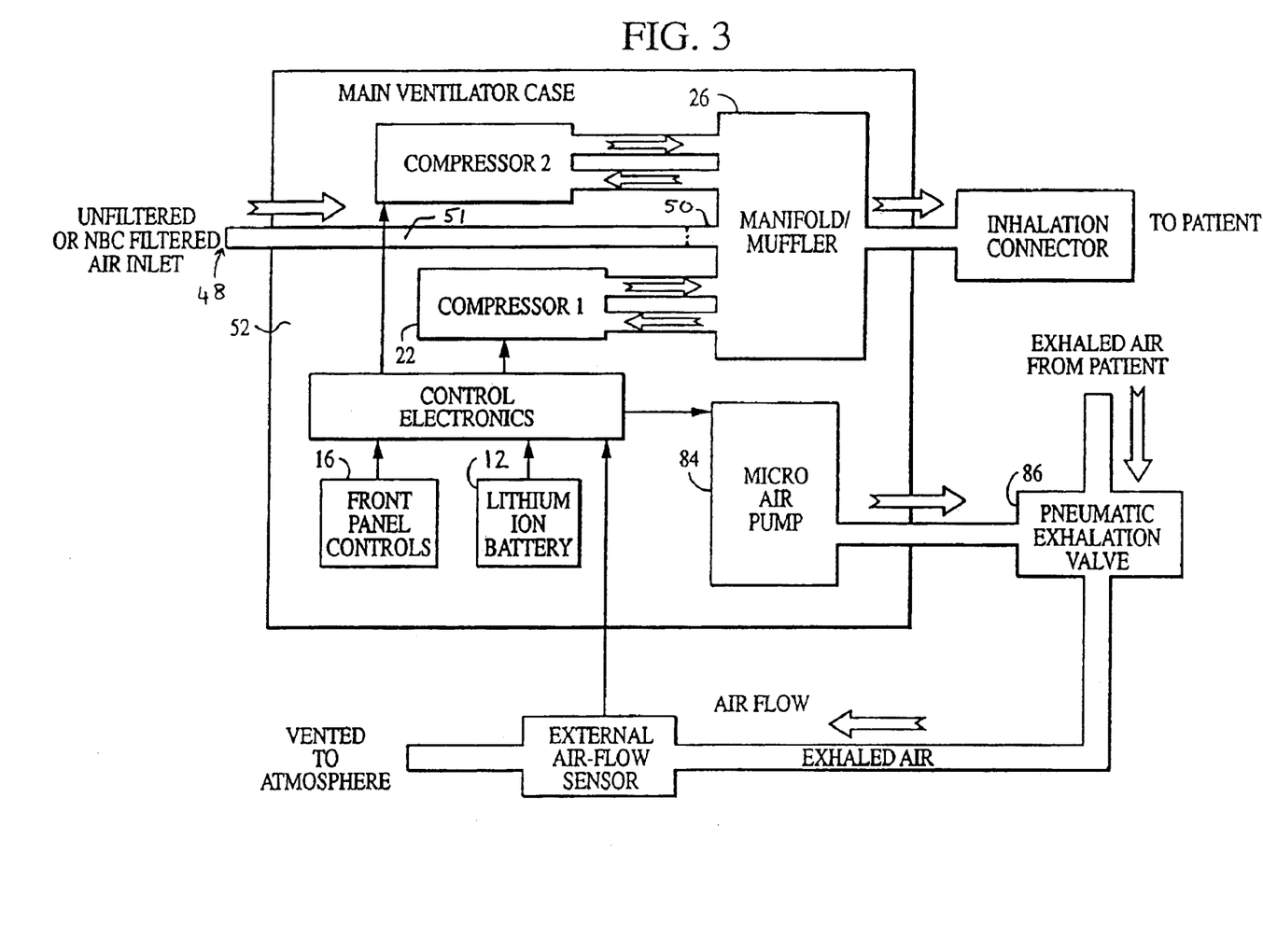
FIG. 3 is a flow chart illustrating the principle of operation of the device of FIG. 1.

The inventive portable ventilator 10, as illustrated in FIGS. 1–6, can be used in the field when a victim/patient, further referred to as an air recipient, requires temporary respiratory relief, as well as in a clinical environment. The insignificant minimal weight of the ventilator of about 4.5–5.5 pounds, its compact structure, and a local source of power 12, such as, for example, a lithium ion battery 12, all provide for the easy transportation of a great number of such devices to a scene associated with multiple victims. The battery 12 can power the device for at least about one hour. In addition, the ventilator 10 can be successfully used as a stationary unit coupled to an external source of power such as, for example, a car battery or any other conventional power supply, through hookups 14 located on a front panel 16 (FIG. 1).

Figure 4:
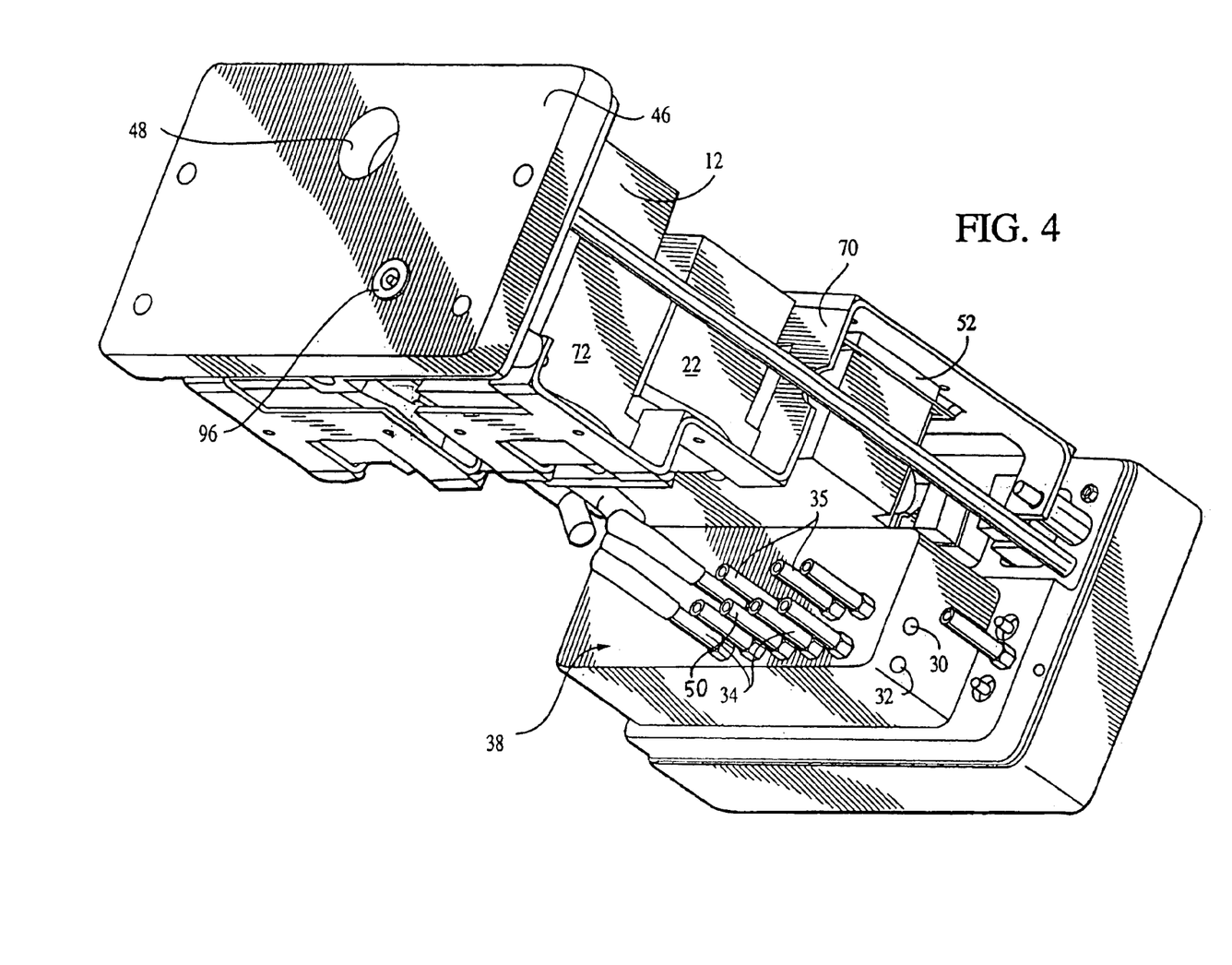
FIG. 4 is a bottom/side perspective view of the inventive device, as illustrated in FIG. 2.
Figure 6:
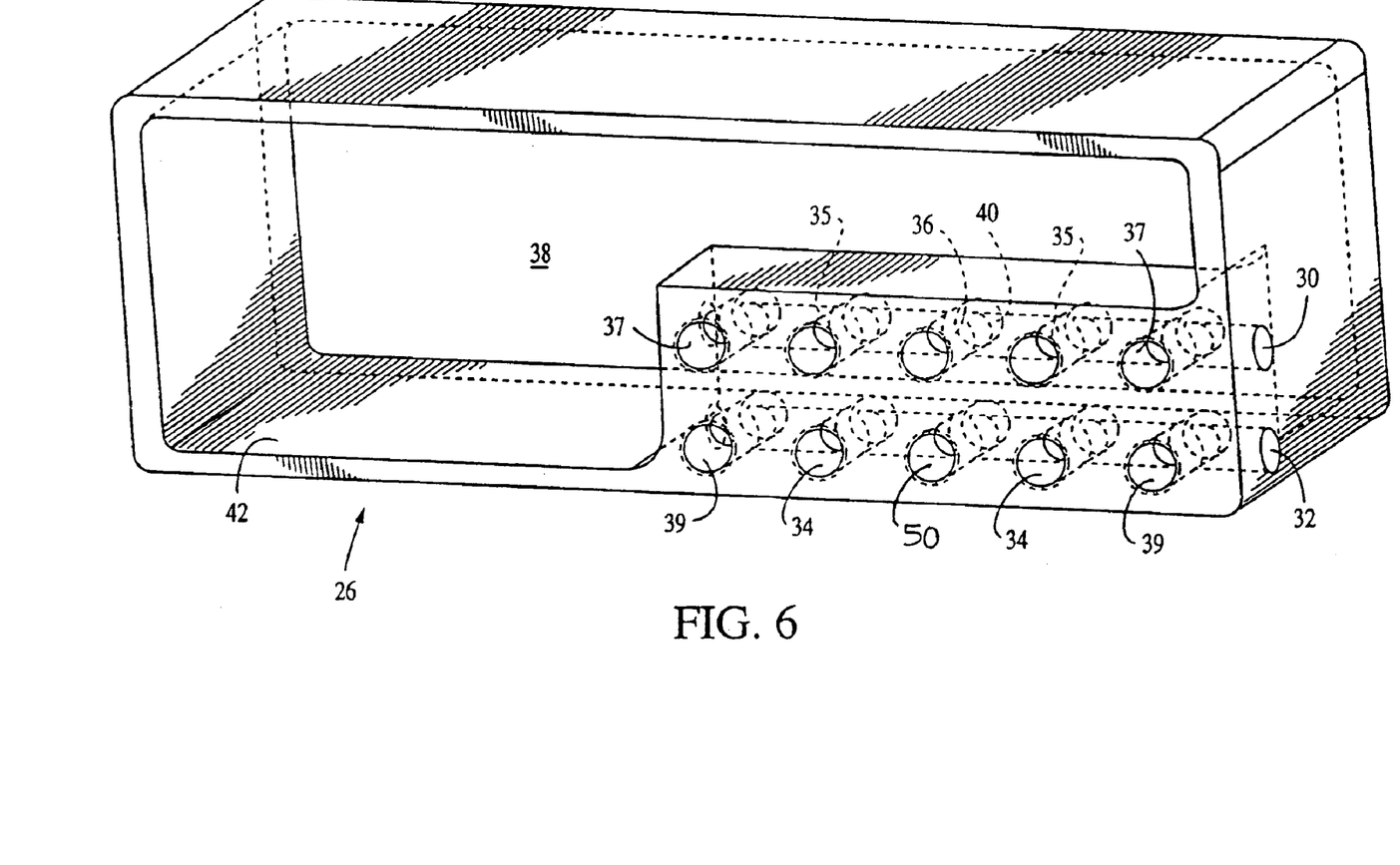
FIG. 6 is an elevated partially broken view of the muffler/accumulator assembly shown in FIG. 5.

In use, the operator, based on such factors as, for example, the condition, age, body type and gender of the air recipient, manipulates a rotary switch 20 to set the desired volume of compressed air to be delivered and further displaces an on/off switch 18 in an "on" position to provide actuation of at least a first compressor 22 (FIG. 2). Energization of the compressor 22 establishes inflow of outer air through an inlet port 48 (FIGS. 1 and 4), located on a back panel 46 of the device 10, via a straight inlet conduit 50 (FIG. 2), which is connected to inlet port 48 via a tube 51 (best shown in FIG. 3, but omitted from FIG. 2 so as to not obscure other parts depicted in FIG. 2), into a first or inlet manifold 32. The latter is configured as a tube having a longitudinal axis, which extends substantially perpendicular to the inlet conduit 50, and provided with at least two outlets. The outlets are in flow communication with opposite chambers of the compressor 22 via substantially straight, uniformly dimensioned conduits 34 that may be configured to have at most one elbow (FIGS. 4 and 6). Following the air path within the device 10, compressed air is directed along a patient ventilation circuitry including substantially straight uniform conduits 35 (FIGS. 4 and 6) and a second or outlet manifold 30 extending parallel to the inlet manifold 32 and provided with a short outlet duct 36. The latter is substantially shorter than and extends parallel to conduits 34, 35 and 50 and opens into a single expansion chamber muffler or accumulator 38 (FIGS. 4 and 5). Finally, air is advanced from the accumulator 38 via the inhale port 44 located on the front panel 16 (FIG. 1) to the air recipient's lungs. An electronic controller 52 (FIG. 4) monitors the operator-selected parameters, such as the desired volume of compressed air, during the compressor's "on" cycle. Switching the compressor 22 between "on" and "off" states generates a strong acoustic signal, which can negatively affect the air recipient, and if produced by multiple ventilators 10 simultaneously, when the help is rendered to many people, becomes more than a nuisance. In accordance with the invention, manifold/muffler assemblies located at opposite upstream (inlet) and downstream (outlet) ends of air path achieve the decrease of the compressor-generated sound and airflow-generated sound. The reduction of the airflow-generated noise is achieved by configuring the conduits 34, 35 and 50 substantially free from contractions and expansions and extending parallel to one another, as well as by positioning the compressor 22 and the accumulator 38 in a close spaced relationship.

A downstream manifold/muffler assembly 26, in addition to minimizing the compressor-generated and air-connector generated sound, is configured to smooth airflow entering the air recipient and eliminate the pulsations therein. Configured of the manifold 30, duct 36 and the single-expansion chamber muffler 38, the assembly is most effective when structured in accordance with the principles summarized in Beranek's paper.

Figure 9:
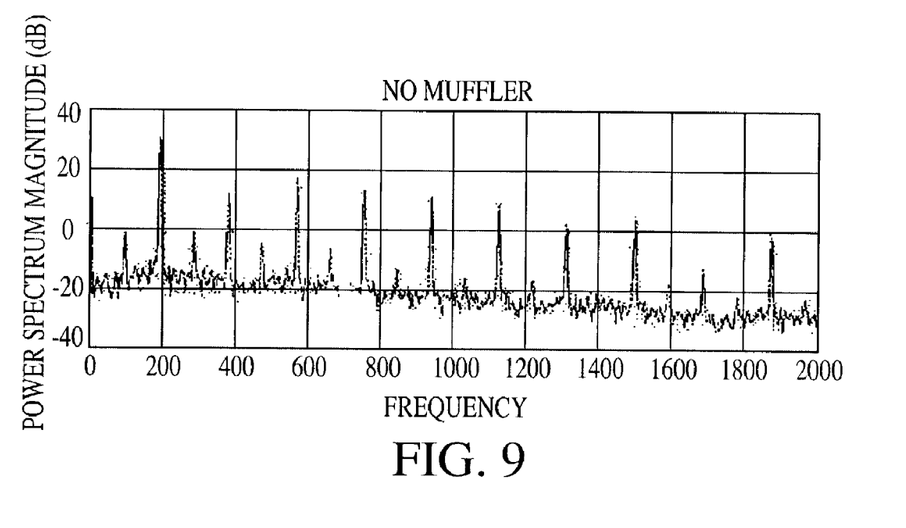
FIGS. 9 and 10 are graphs illustrating power spectral density of sound at the outlet end of the device shown in FIG. 1 with the muffler/accumulator assembly shown in FIG. 4 without and with the assembly, respectively.
Figure 10:
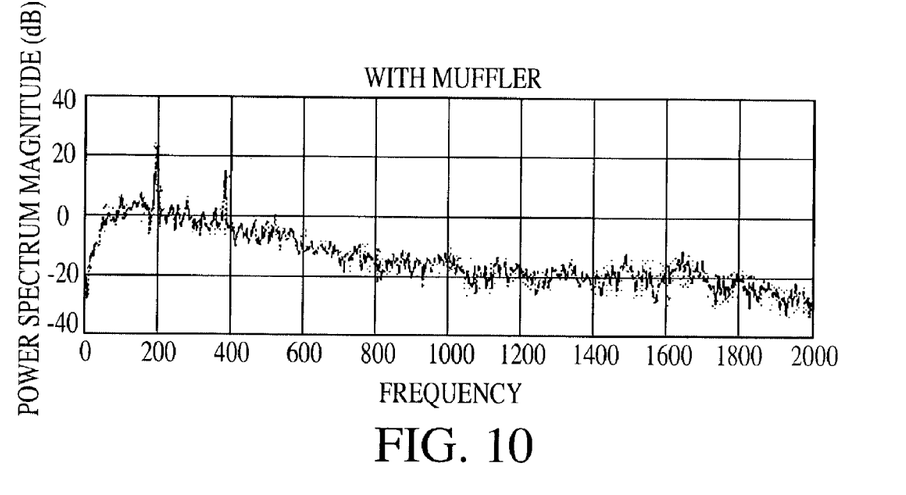

Structurally, the muffler/accumulator assembly 26 is a single expansion chamber structure enclosed in a housing 42 (FIGS. 4 and 5) juxtaposed with the compressor 22 and sealingly coupled to the front panel 16 of the ventilator 10. The manifold 30 is configured as an elongated tube, which is provided with numerous ports receiving the conduits 35 (FIGS. 4 and 5) traversed by compressed air, and the duct 36 provided with a manifold outlet 40 opening into the single expansion chamber of the muffler 38. The shape of the muffler 38 can be either cylindrical or rectangular depending on the configuration of the device 10. The dimensions of the muffler vary as a function of size and the amount of reductions achieved for a specified volume when using the equations as disclosed in Beranek's paper. The rectangular muffler 38, as illustrated in FIGS. 2–6, is advantageously about 3–4" long, about 3.5" wide and about 1.25" thick. Mufflers of such dimensions were found to almost completely eliminate the loud compressor sound from the tubing. Alternatively, instead of the rectangular muffler, the cylindrical muffler, having substantially the same volume as the rectangular one and dimensioned to have a diameter of about 2.5" and a length of about 3–4", produces equally satisfactory sound-deadening effects. The sound at the downstream end of the air output path circuit was recorded with and without the muffler 38. FIGS. 9 and 10 show the power spectral density of these sound recordings. FIG. 9 illustrates the plot corresponding to the sound with no muffler present, whereas FIG. 10 shows the drastically reduced magnitude of the compressor-generated sound upon installation of the inventive manifold/muffler assembly 26.

According to Beranek's publication, the Transmission Loss of the sound is greatest when the m parameter is 100 or higher. Since ¼ in tubing is used before and after the muffler, it was decided to design the cylindrical muffler to have a diameter of about 2.5 in. This gives an m parameter value of about 100. Advantageously, based on experiments, the m parameter varies between about 100 and about 200. Empirical data shows that choosing m=140 allows to lessen the volume needed for the muffler to 12 cubic inches. Furthermore, selection of transmission loss of about 21 dB eliminates the pulsations. The manifold/muffler assembly 26 is designed to have a maximum amount of transmission loss at a wide range of frequencies below and above 200 Hz. To accomplish this, advantageously the kl parameter varies from about 0.1 to about 0.4 and, thus, fits the requirement of less than 0.8 corresponding to a transmission loss of around 19 to 24 dB.

Figure 7:
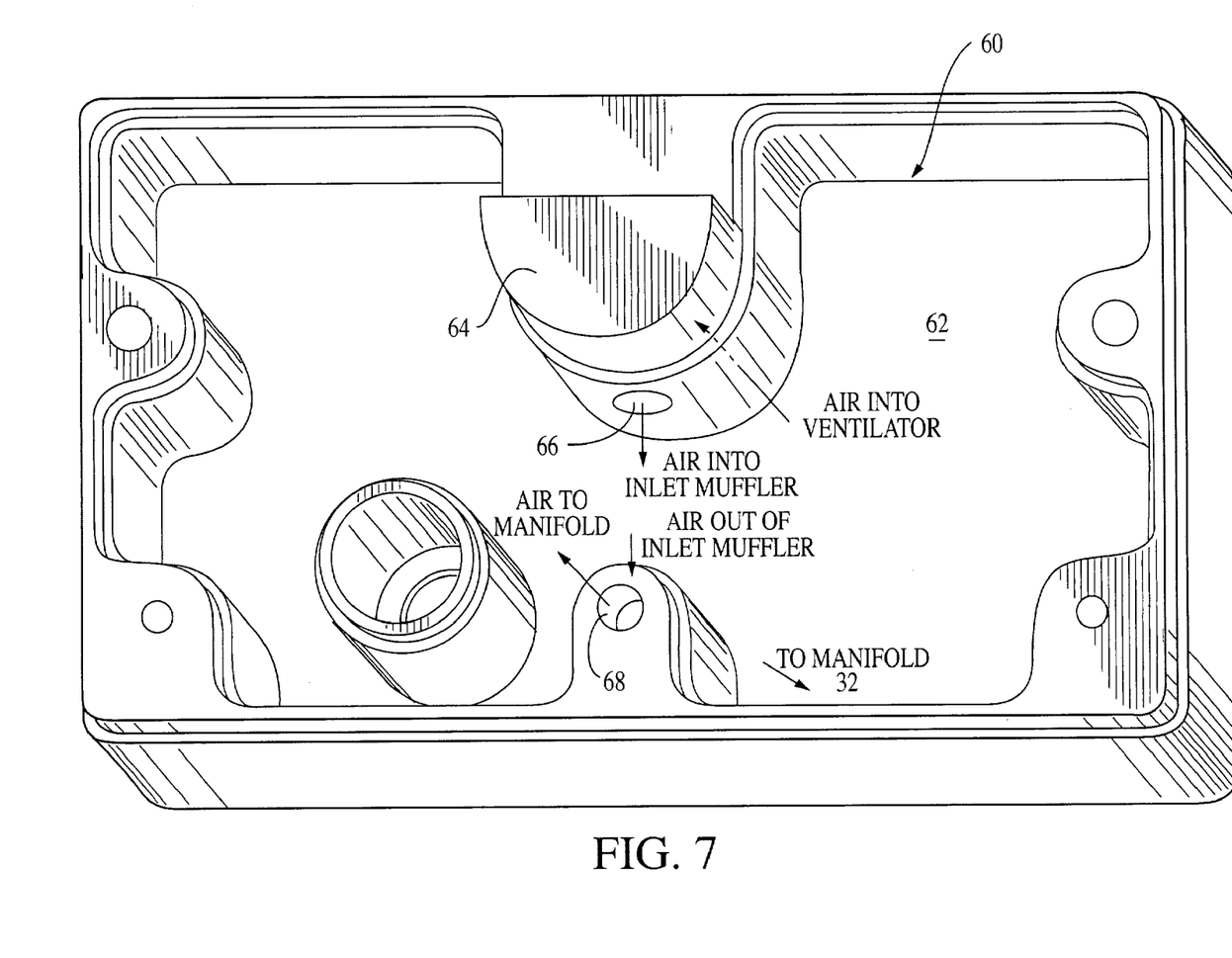
FIG. 7 is a view of back panel of the inventive device of FIG. 1 provided with an inlet muffler assembly shaped and dimensioned in accordance with the inventive concept.
Figure 8:
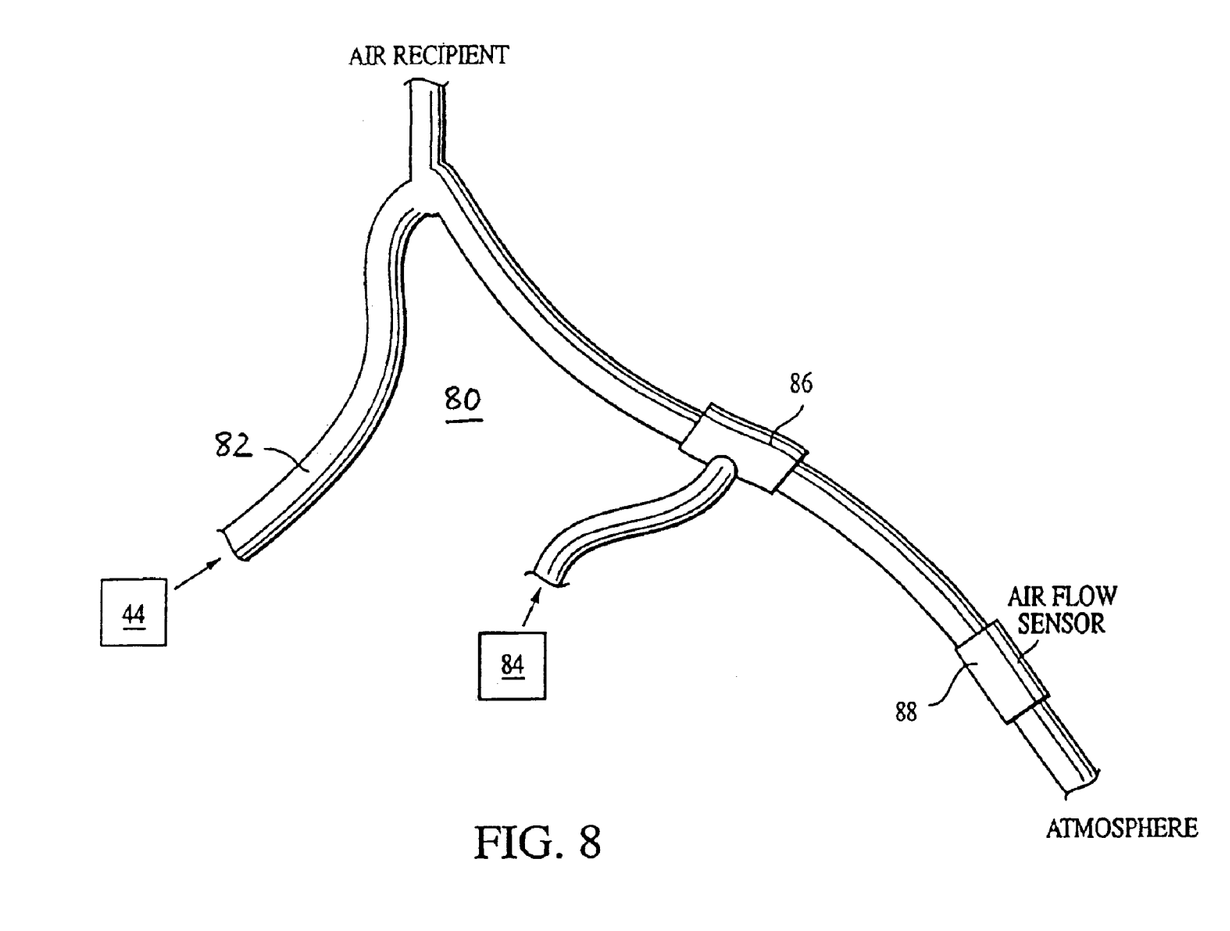
FIG. 8 is a schematic view of a disposable respiratory portion of a kit including, besides the disposable respiratory portion, the inventive device of FIG. 1.

Referring to FIGS. 2 and 7, further reduction of the sound signal is achieved by providing the upstream or inlet manifold/muffler assembly 60 formed in the back panel 46 of the device 10. The back panel 46 is formed with a muffler 62 configured as a chamber of a sufficient depth. Although the geometry of the chamber can vary, one of its configurations includes a U-shape peninsula 64 having an upstream duct 66, which is in flow communication with the air inlet 48 (FIG. 2). Ambient air, forced through the air inlet 48 in response to the actuation of the compressor 22, flows through the upstream duct 66 into the muffler 62 and, further, through an outlet duct 68 towards the patient ventilation circuit. The upstream duct 66 and the chamber of the muffler 62 are shaped and directed to meet the requirements of Beranek's publication. Preferably, the outlet duct 68 is configured similarly to the inlet duct 66.

Structural integrity of the device 10 is achieved by utilizing a mounting plate 70 (FIG. 2) configured to support the electronic controller 52 and the first compressor 22. Configuration of the device allows for an auxiliary compressor 72 coupled in parallel to the first compressor 22 to be mounted to the mounting plate 70 without taking on an additional space. The compressors 22 and 72 can be switched on simultaneously by the electronic controller 52 if the desired volume, set by the operator, exceeds a given reference value. Due to the geometry of the air conveying manifold/muffler assemblies 26 and 60 including relatively short air-paths, which are practically free from elbows, contractions and expansions, no "fighting" between the compressors 22 and 72 has been observed. To provide flow communication between the second compressor 72 and the manifold/muffler assembly 26, the device 10 features additional two inlet conduits 39 and two outlet conduits 37 (FIG. 6). The former two convey incoming air from the inlet manifold 32 into the mixing chambers of the compressor 72, whereas the outlet conduits 37 convey compressed air from the compressor's expansion chambers towards the outlet manifold 30 of the manifold/muffler assembly 26.

Figure 5:
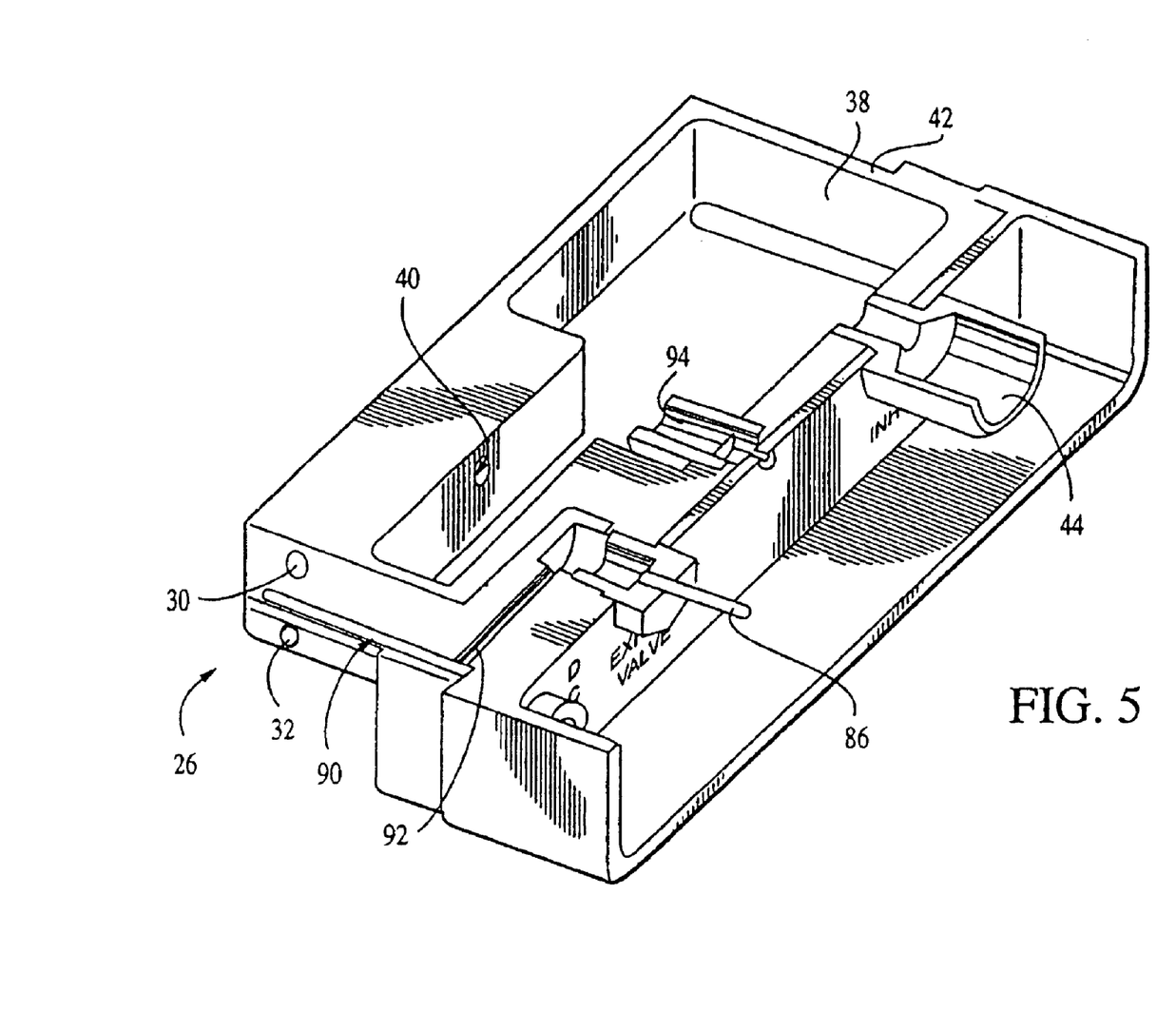
FIG. 5 is a perspective view of a muffler/accumulator assembly of the inventive device.

The compressors, which are actuated during the inhale stroke of the air recipient, are turned off automatically based on the desired volume of compressed air delivered into the air-recipient's lungs. Turning to FIGS. 1–3 and 8, a disposable air conveying system 80 (FIG. 8) delivers the compressed air to the air recipient through a first flexible tube 82 coupled to the inhale port 44 (FIG. 2). As the compressor completes its "on" mode of operation, the electronic controller 52 (FIG. 2) actuates a micro air pump 84 (FIG. 3) opening a one-way pneumatic exhalation valve 86 to allow for the exhale stroke of the air recipient during which wasted gases are vented to atmosphere through the exhalation valve 86. Structurally, as seen in FIG. 5, the side of the manifold/muffler 26 has a channel 90 leading from the micro air pump 84 to the exhalation valve 86 through a conduit 92 formed in the rear wall of the panel 16. Actuation of the micro pump generates pressure sufficient to open the exhalation valve 86 allowing wasted gases to escape into the atmosphere. Exhalation continues until an airflow sensor 88 (FIG. 1) located on the front panel 16 senses airflow. Zeroing out of the flow rate triggers actuation of the compressor(s) 22, and a duty cycle corresponding to the inhale stroke is repeated. To prevent overpressurization of the air recipient's lungs, a safety valve 94 (FIGS. 1 and 2) provided on the front panel 16, opens immediately if a reference value has been exceeded (FIGS. 1 and 5). Specific locations of the inhale port 44 is illustrated in FIGS. 1–6 for purely illustrative purposes and can be changed. One of the possibilities is to form the inhale port in alignment with the manifold outlet 40 of the outlet manifold/muffler assembly 26.

The device 10 can be used for a prolonged period of time by recharging the battery 12 or by providing external power. For this purpose, as shown in FIG. 4, the back panel 46 is provided with an adapter 96 (FIG. 4) allowing coupling of the device to an external charging source. If the device 10 is used in contaminated atmosphere, the air inlet 48 can be provided with a removably connectable to filter 98, as illustrated in FIG. 2. Reduction in vibration can be achieved by implementing vibration mounts 100 (FIG. 2) coupling the front 16 and back 46 panels to the mount plate 70. To assure that the malfunction of the inventive device does not go undetected, a sound generator (not shown) can be removably mounted on the back panel 46 and coupled to the electronic controller 52 and the rechargeable battery 12.

The inventive device 10 has a simple, cost-efficient and substantially noise-free structure providing the air recipient with smooth, uniform airflow. The ventilator can be distributed as part of a kit including, besides the ventilator itself, the filter 98 (FIG. 2), the disposable conveying system 80 providing flow communication between the ventilator and the air-recipient and a sound source. While the invention has been disclosed with respect to preferred embodiments, various changes can be made without departing from the scope of the invention as defined by the appending claims.

What is claimed is:

1. A portable ventilator for providing an air-recipient with compulsory inspiration, comprising:
   at least one compressor for controllably supplying compressed air along an output air path of the ventilator in an upstream to downstream direction towards the air recipient;
   an outlet manifold located along the ventilator output air path downstream from the at least one compressor and in direct flow communication therewith; and
   a single-expansion-chamber outlet muffler located along the ventilator output air path downstream from the outlet manifold and in direct flow communication with the air-recipient and with the manifold outlet, whereby the compressed air from the compressor passes through the manifold outlet, the muffler and then an inhale port of the muffler toward the air-recipient, the muffler and the manifold outlet being configured so that airflow through the inhale outlet port of the muffler is substantially pulse free and a transmission loss, defined as the ratio of sound power generated by the at least one compressor and incident on the outlet muffler to the sound power transmitted by the muffler, is sufficient to deaden the sound power of the at least one compressor.

2. The portable ventilator of claim 1, wherein the outlet muffler and the outlet manifold form an outlet one-piece manifold/muffler assembly, which further comprises an inlet manifold located upstream from the at least one compressor so as to be traversed by incoming outer air that is to be compressed by the at least one compressor, wherein the inlet manifold is configured to supply the incoming air to an input of the compressor.

3. The portable ventilator of claim 2, wherein the at least one compressor is juxtaposed with the outlet manifold, the ventilator further comprising a plurality of substantially straight, short and uniformly dimensioned air-conveying conduits extending between and in flow communication with the at least one compressor and the outlet manifold.

4. The portable ventilator of claim 2, further comprising a front panel coupled to the one-piece manifold/muffler assembly and provided with the inhale outlet port, and a back panel spaced from the front panel and provided with an air inlet port, which is configured to be traversed by incoming air in response to actuation of the at least one compressor and is in flow communication therewith through the inlet manifold.

5. The portable ventilator of claim 4, further comprising a mount plate coupled to the front and back panels and supporting at least one compressor, and a controller coupling the at least one compressor with a power source and operative to actuate the at least one compressor so as to supply a desired volume of compressed air through the outlet of the outlet manifold, the muffler and via the inhale port to the air recipient during an inspiration stroke thereof.

6. The portable ventilator of claim 5, further comprising a volume regulator coupled to the controller and operative to set a reference value, below which the at least one compressor operates in a low-volume mode of operation of the portable ventilator.

7. The portable ventilator of claim 5, wherein the power source is either internal or external, the internal power source being a rechargeable battery provided with an adapter connectable to the external power source and located on the back panel.

8. The portable ventilator of claim 6, further comprising an auxiliary compressor detachably mounted on the mount plate and coupled with the controller so that the at least one and auxiliary compressors produce high volume of compressed air delivered to the air recipient through the outlet of the outlet manifold, the muffler and via the inhale port in response to a signal generated by the volume regulator and exceeding the reference value.

9. The portable ventilator of claim 6, wherein the at least one and auxiliary compressors operate in parallel.

10. The portable ventilator of claim 6, further comprising an one-way exhale valve mounted on the front panel and coupled to the controller to provide flow of wasted gases from the air recipient during an expiration stroke thereof.

11. The portable ventilator of claim 10, further comprising a micro air pump coupled to the controller and in flow communication with an outlet of the one-way exhale valve to create a pressure sufficient to open the one-way exhale valve in response to a control signal generated by the controller upon termination of airflow from the at least one compressor via the outlet of the outlet manifold and through the muffler during the inspiration stroke of the air recipient.

12. The portable ventilator of claim 11, further comprising a flow control sensor coupled to the controller and operative to determine termination of airflow during the inspiration stroke and to output a signal in response to which the controller generates the control signal activating the micro air pump.

13. The portable ventilator of claim 10, further comprising a safety valve operative to bleed in response to a build-up pressure exceeding a reference value to prevent the lungs of the air recipient from overpressurization.

14. The portable ventilator of claim 4, further comprising an inlet manifold/muffler assembly including
a respective single-chamber muffler in flow communication with at least one compressor, and
an upstream manifold providing flow communication between the air inlet port and the single-chamber muffler of the inlet manifold/muffler assembly,
the inlet manifold/muffler assembly being formed in the back panel and being configured substantially identically to the outlet manifold/muffler assembly to reduce the transmission loss upstream from the at least one compressor.

15. The portable ventilator of claim 1, wherein the transmission loss is calculated in terms of two parameters m and kl calculated according to the following:

$$L_{TL} = 10\log\left[1 + \frac{1}{4}\left(m - \frac{1}{m}\right)^2 \sin^2 kl\right],$$

wherein the parameter m is the ratio of the cross-sectional area of the single-chamber muffler to the cross-sectional area of inlet opening and the parameter kl is given as a ratio of 2 pi times the length of the muffler divided by the wavelength according to the following:

$$kl = \frac{2\pi l}{\lambda}$$

16. The portable ventilator of claim 15, wherein the parameter m ranges between 100 and 200 and the parameter kl varies from 0.1 to 0.4 to achieve a transmission loss of around 19 to 24 dB.

17. A portable ventilator, comprising:
spaced front and back end plates;
at least one compressor located between the front and back end plates and operative to generate airflow along a path;
an inlet manifold/muffler assembly provided in the back panel and configured to be traversed by incoming air in response to actuation of the at least one compressor; and
an outlet manifold/muffler assembly coupled to the front panel and traversed by air flow directed towards an recipient, the inlet and outlet manifold/muffler assemblies having each a single-chamber muffler and an inlet opening located upstream from and in direct flow communication with a respective single-chamber muffler, wherein the inlet and outlet manifold/muffler assemblies are configured to decrease an acoustic signal generated by the at least one compressor along upstream and downstream ends of the path and to provide smooth constant airflow to the air recipient, wherein the inlet manifold/muffler assembly includes a casing mounted to the front panel and including an upstream compartment which houses inlet and outlet manifolds, the inlet manifold located upstream from the at least one compressor and being in flow communication therewith and with the inlet manifold/muffler assembly, the outlet manifold formed with inlet opening of the being located downstream from the at least one compressor.

18. The portable ventilator of claim 17, wherein the back end plate is configured to form the single-chamber muffler of the inlet manifold/muffler assembly and to have a duct traversed by incoming air flow in response to activation of the at least one compressor and having the inlet opening.

19. The portable ventilator of claim 18, wherein the inlet and outlet manifold/muffler assemblies are each configured so that a transmission loss, defined as the ratio of sound power generated by the at least one compressor and incident on a respective single-chamber muffler to the sound power transmitted by the muffler, is sufficient to deaden the sound power of the at least one compressor.

20. The portable ventilator of claim 18, wherein the transmission loss is calculated in terms of two parameters m and kl calculated according to the following:

$$L_{TL} = 10\log\left[1 + \frac{1}{4}\left(m - \frac{1}{m}\right)^2 \sin^2 kl\right],$$

wherein the parameter m is the ratio of the cross-sectional area of the single-chamber muffler to the cross-sectional area of manifold opening into the and the parameter kl is given as a ratio of 2 pi times the length of the muffler divided by the wavelength according to the following:

$$kl = \frac{2\pi l}{\lambda}$$

21. The portable ventilator of claim 20, wherein the parameter m ranges between 100 and 140, the parameter kl varies from 0.1 to 0.4.

22. The portable ventilator of claim 17, further comprising an auxiliary compressor operative to be coupled in parallel to the at least one compressor.

23. The portable ventilator of claim 17, wherein the at least one compressor is juxtaposed with the outlet manifold/muffler assembly, which further includes a plurality of substantially straight, short and uniformly dimensioned air-conveying conduits providing air communication between the at least one compressor and the outlet manifold.

* * * * *